(12) United States Patent
Dal Molin

(10) Patent No.: US 7,663,451 B2
(45) Date of Patent: Feb. 16, 2010

(54) RF TELEMETRY FOR AN ACTIVE MEDICAL DEVICE SUCH AS AN IMPLANT OR PROGRAMMER FOR AN IMPLANT

(75) Inventor: Renzo Dal Molin, Châtillon (FR)

(73) Assignee: ELA Medical S.A.S., Montrouge (FR)

( * ) Notice: Subject to any disclaimer, the term of this patent is extended or adjusted under 35 U.S.C. 154(b) by 209 days.

(21) Appl. No.: 11/757,252

(22) Filed: Jun. 1, 2007

(65) Prior Publication Data
US 2007/0279149 A1 Dec. 6, 2007

(30) Foreign Application Priority Data
Jun. 2, 2006 (FR) .................................. 06 04933

(51) Int. Cl.
*A61N 1/08* (2006.01)
*A61N 1/16* (2006.01)
*H03H 9/70* (2006.01)
*H03H 9/54* (2006.01)

(52) U.S. Cl. .................. 333/133; 333/188; 333/189; 333/190; 607/32; 607/60

(58) Field of Classification Search .................. 333/133, 333/187–189, 190; 607/60, 32
See application file for complete search history.

(56) References Cited
U.S. PATENT DOCUMENTS

| | | | |
|---|---|---|---|
| 5,714,917 A | 2/1998 | Ella | |
| 6,657,517 B2 * | 12/2003 | Barber et al. | 333/187 |
| 6,670,866 B2 * | 12/2003 | Ella et al. | 333/133 |
| 6,741,146 B2 * | 5/2004 | Ella | 333/133 |
| 6,868,288 B2 | 3/2005 | Thompson | |
| 6,927,649 B2 * | 8/2005 | Metzger et al. | 333/133 |
| 7,106,148 B2 * | 9/2006 | Kawamura | 333/133 |
| 7,126,440 B2 * | 10/2006 | Bradley et al. | 333/133 |
| 7,180,224 B2 | 2/2007 | Bouche et al. | |
| 7,194,247 B2 * | 3/2007 | Tikka et al. | 455/339 |
| 7,310,029 B2 | 12/2007 | Robert et al. | |
| 2004/0140869 A1 | 7/2004 | Marksteiner et al. | |
| 2005/0068124 A1 * | 3/2005 | Stoemmer | 333/189 |
| 2006/0279381 A1 * | 12/2006 | Frank | 333/189 |

* cited by examiner

*Primary Examiner*—Barbara Summons
(74) *Attorney, Agent, or Firm*—Orrick Herrington & Sutcliffe, LLP

(57) ABSTRACT

RF telemetry for an active medical device such as active implant or programmer for such implant. The device includes at least one RF antenna (14), and at least one RF telemetry transmitter/receiver (44) with, for coupling to the antenna, an associated band rejection filter (54). The band rejection filter (54) comprises at least one volume acoustic wave BAW resonator (40) of the SMR type with insulation by Bragg acoustic reflector (42). The device can be a multi-band device comprising a plurality of RF transmitters/receivers (12, 44) operating in respective distinct bands of frequencies such as the 402~405-MHz, 863~870-MHz, 902~928-MHz and 2.4-GHz bands or by UWB transmission.

12 Claims, 4 Drawing Sheets

RF TELEMETRY FOR AN ACTIVE MEDICAL DEVICE SUCH AS AN IMPLANT OR PROGRAMMER FOR AN IMPLANT

The present invention relates to an active medical device as such devices are defined by the Jun. 14, 1993 93/42/CE directive of the Counsel of European Communities, and more particularly to active implantable medical devices as such devices are defined by the Jun. 20, 1990 90/385/CEE directive of the Counsel of European Communities.

These devices include devices that are intended to monitor cardiac activity and generate pulses for pacing, resynchronization, defibrillation and/or cardioversion in response to a rhythm disorder detected by the device. It also includes neurologic devices, pumps for the diffusion of medical substances, cochlear implants, implanted biological sensors, etc., as well as devices for pH measurement or intracorporal impedance measurement (such as the measurement of transpulmonary or intracardiac impedance). One will also note that, although this invention is particularly advantageous for implementation in implanted devices, such as pacemakers, cardioverters or defibrillators, it can as well be implemented with non-implanted medical devices, for example, data recorders for monitoring ambulatory patients and recording certain physiologic parameters such as external Holter devices that monitor cardiac activity.

BACKGROUND OF THE INVENTION

Generally, most active medical devices are designed so as to allow data exchanges with a "programmer," an external apparatus used to check the parameter settings of the device, read information recorded thereby or write information thereto, or update the internal software for driving the device.

Such a data exchange between the medical device and the programmer is operated by telemetry, i.e. a technique of remote transmission of information, without galvanic contact.

Up to now, telemetry for implanted devices used to be essentially performed by magnetic coupling between a coil of the implanted device and a coil of the programmer (or programming head), a technique known as the "induction technique". However, that technique, due to the very short range of inductive coupling, has the shortcoming of requiring the use of a "telemetry head" or wand linked to the programmer and containing a coil that an operator puts in the proximity of the site where the device is implanted.

Recently, another technique has been proposed implementing a non-galvanic coupling using the two components of an electromagnetic wave produced by transmitter/receiver circuits operating within the radiofrequency (RF) domain, typically with frequencies ranging around several hundreds of Megahertz. That technique, known as "RF telemetry", allows one to program or interrogate implanted devices from distances greater than 3 m, and therefore allows the exchange of data without the need for using a telemetry head, and even without the intervention of an external operator. A device comprising means of RF telemetry and associated programmer, are, for example, described in U.S. Pat. No. 6,868,288 (Thompson).

A satisfactory functioning of RF telemetry circuits implies an efficient elimination of RF parasites that are likely to produce interference and disturb data transmission. Indeed, differently from induction techniques, which present a good immunity against parasites, the RF signal reception is strongly disturbed by the electromagnetic environment, notably radio signals, TV and mobile phone signals, and also the numerous industrial parasites likely to be produced within the immediate surroundings of a patient implanted with a device.

RF telemetry circuits therefore require the use of very efficient band-pass filters, presenting a very abrupt band rejection characteristic. Acoustic wave filters present such characteristics, and Thomson U.S. Pat. No. 6,868,288, cited above, precisely proposes to use, in the RF telemetry circuit of an implantable device, a Surface Acoustic Wave resonator (SAW) or a Thin Film Bulk Acoustic Resonator (FBAR). Such resonators are indeed well known for their characteristics presenting a very high selectivity, and for their use in the realization of very efficient band-pass filters.

Those SAW or FBAR resonator filters however present a few shortcomings, especially when they are used in implanted devices. Indeed, SAW resonators use, by principle, the surface propagation of an acoustic wave, which correlatively implies a relatively large component size. This shortcoming is particularly embarrassing when it comes to implanted devices, which, as it can be easily understood, require an advanced downsizing of electronic circuits, due to the small available space within their cases.

Also, from a technological point of view, these SAW resonators are only available as discrete components that must be bonded onto the electronic circuit of the implant, with consequent shortcomings, notable in terms of additional steps as part of manufacturing processes and a higher cost.

Finally, from the electrical point of view, SAW resonators present an excellent selectivity, but introduce significant insertion losses in the circuits in which they are used, consequently affecting the sensitivity of the telemetry receiver.

Differently from SAW resonators, FBAR resonators present a much smaller size and lower insertion losses. However, these FBAR resonators are more difficult to make, for they require micro-machining of a very thin movable membrane, likely to become resonant (one will describe more in details the structure of FBAR resonators by reference to FIGS. 2a and 2b). That micro-machining is difficult to implement, notably as part of a collective process, which introduces much scrap during manufacturing of the components.

Besides, the movement of the movable membrane implies that a free space exists below and above it. For that reason, if any particles (such as dust) were to deposit above the membrane during or after the manufacturing process, the resonance frequency thereof would be modified, and it would be necessary to re-tune the filter. So as to palliate this shortcoming, once the component has been made and adjusted in terms of frequency, it has to be enclosed in a hermetic volume, with the forming of an additional layer, or bonding of a closure cap for the component.

From an industrial point of view, though it is theoretically possible to integrate the FBAR resonator along the manufacturing process of the circuit it is associated with, such an integration is practically difficult to implement with a satisfactory yield, which is the reason why the FBAR resonators available nowadays are only available in the form of discrete components. The FBAR component must therefore be bonded onto the electronic circuit or onto the hybrid board through an additional process such as wire-bonding or flip-chip, which, similarly to the case of SAW resonators, dramatically increases manufacturing cost and reduces electrical performances due to the presence of wires, conductive pathways, etc.

Apart from the difficulty to find and sustain the tuning of an FBAR resonator, this latter presents a rejection characteristic less abrupt than that of a SAW resonator. Thus, to obtain a satisfactory rejection level, it is necessary to combine together a plurality of FBAR resonators. Such a multiplication of components consequently increases cost, volume and difficulties for developing the final circuit.

OBJECTS AND SUMMARY OF THE INVENTION

It is therefore an object of the present invention to realize an active medical device, and/or its associated programmer, comprising RF telemetry circuits with no FBAR resonators, that palliate all the shortcomings cited above, and that are moreover advantageously adapted to the specific constraints of active implants, which require a more advanced miniaturization of the electronic circuit, provided the small volume of free space that is available within the implant's case.

The purpose of this invention is preferably to realize such a device and/or programmer, the RF circuits of which present the following advantages:
  low manufacturing cost,
  a potentially integrable filter, so as to obtain a monolithic component including the RF transmitter/receiver chip along with its associated band rejection filter. Such an integration presents many advantages: the overall cost reduction, reduction of insertion losses and maximization of the useful area (so as to miniaturize implants, it is known, nowadays, to stack many monolithic chips with one on top of the others);
  possible collective manufacturing with a good yield of the manufacturing process (minimum scrap);
  reduction of parasite impedances, notably inductances (conductors, conductive pathways, bondings, etc.), allowing to reduce the insertion losses and prevent from having to retune the filter after the integration or bonding on the circuit;
  possibility to use a plurality of resonators, allowing to design competitive filters combining a plurality of resonators allowing to obtain a very abrupt characteristic.

Another purpose of this invention is to propose an active device comprising RF telemetry circuits likely to operate in different bands of frequencies, such as MICS band (Medical Implants Communication System) 401~402 MHz, 402~405 MHz, 405~406 MHz, or standardized public ISM bands (Industrial, Scientific and Medical) 863-870 MHz, 902~928 MHz and 2.4 GHz used by medical devices, or a transmission of the UWB (Ultra Wide Band) type, a technique following which the transmitted signals are Dirac pulses producing in the frequency domain, a very large spectrum.

Indeed, the current devices equipped with RF telemetry functions are all merely multi-channel devices, that is: using numerous frequencies that are all within a same band.

However, it would be particularly advantageous to propose a multi-band device (bi-band, tri-band, or even quad-band), because:
  the authorized frequency bands are not necessarily the same in different countries;
  according to the circumstances, the propagation may be better in one band than another, and it would be advantageous to allow choosing that band that has the best propagation so as to optimize data transmission,
  the band workload (number of channels used) varies according to the different bands, and again, it would be advantageous to choose a band presenting a sufficient number of free channels.

The technical problem solved by the present invention, and the different purposes cited above are reached, by an active medical device, or its associated programmer, of the standard type, comprising, as taught in Thompson U.S. Pat. No. 6,868,288 cited above, at least one RF antenna and at least one RF telemetry transmitter/receiver with, for coupling to the antenna, an associated band rejection filter, such device being characterized, in accordance with the present invention, in that the band rejection filter includes at least one volume acoustic waves BAW resonator, of the SMR type with Bragg acoustic reflector insulation.

Such a resonator structure is described in published US patent application US 2004/0140869. But this document only proposes to use this component for its higher electrical performances, notably in terms of overvoltage coefficient (Q factor) and coupling coefficient, in order to design filters with a characteristic presenting steeper edges.

In a preferred embodiment, the device of the present invention comprises a plurality of RF telemetry transmitters/receivers operating in respective distinct frequency bands, notably at least two of the following bands: 401-402 MHz, 402-405 MHz, 405-406 MHz, 863-870 MHz, 902-928 MHz or 2.4 GHz, or a transmission of the UWB type. Each transmitter/receiver comprises a respective band rejection filter, at least one of which including at least one volume acoustic waves BAW resonator of the SMR type with an acoustic Bragg reflector insulation.

The device antenna can be common to the different transmitters/receivers, and coupled therewith through band rejection filters and elements of impedance matching.

In an alternate preferred embodiment, it can also be foreseen to include means for evaluating the performance of the different bands of frequencies, and means for selecting, for the transmission of RF telemetry signals, one of the plurality transmitters/receivers operating in that one of the bands that provides the best performance. The means for evaluating performance can notably evaluate one or more of a number of criteria, including without limitation, the received signal level, the maximum rate of data likely to be transmitted, and the workload of the different channels in the respective bands. Yet another alternative is to include means for commuting the transmitter(s)/receiver(s) operating in the non-selected bandwidth(s) towards a low power consumption mode.

Such an active device is typically realized with a hybrid circuit board and at least one monolithic chip circuit, bonded on this board, integrating said RF telemetry transmitter/receiver. The BAW resonator can then be either directly integrated to the chip on its surface, or realized in the form of a discrete component, distinct from the chip, bonded on the surface of that chip or alternately on the surface of the hybrid circuit board.

Very advantageously, the BAW resonator is a tunable resonator, comprising an erodable superficial charge layer that can be trimmed to tune the resonator.

The band rejection filter can be a filter with differential input and output, comprising a plurality of BAW resonators configured as a mesh, or a filter with asymmetric input and output, comprising a plurality of BAW resonators in a ladder configuration.

BRIEF DESCRIPTION OF THE DRAWINGS

Further characteristics, features and advantages of the invention will become more apparent to a person of ordinary skill in the art from a consideration of the following detailed description of a preferred embodiment of the present invention, made with reference to the attached figures, in which the same reference numbers designate same or functionally similar elements from one figure to the next, and in which.

DETAILED DESCRIPTION OF THE INVENTION

Figure 1:
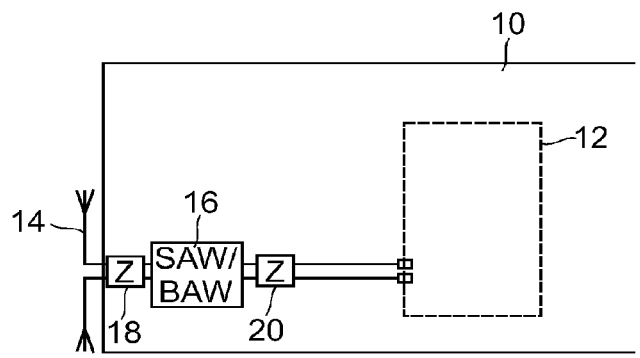
FIG. 1 is a schematic diagram showing an RF telemetry transmitter/receiver coupled with its associated antenna, in the case of a device of the prior art.

With reference to FIG. 1, a schematic representation of the configuration of a RF telemetry circuit of an active medical device following the prior art is shown.

Main circuit 10, typically realized on a hybrid substrate, comprises an RF telemetry transmitter/receiver 12 coupled to an antenna 14 incorporated in the device (for example, in the area of the implant connector head).

The rejection of parasite signals is ensured by interposing, between the antenna 14 and circuits 12, a resonator 16 such as a surface acoustic wave SAW resonator, or volume acoustic wave BAW resonator 16. Components for impedance matching 18, 20 are included, as needed, in order to ensure coupling and potential symmetrization, as well as reduce the insertion losses.

Figure 2A:
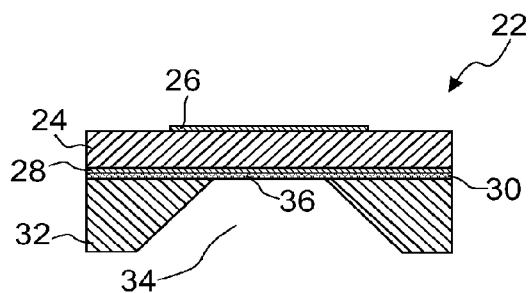
FIGS. 2a and 2b show the principle structure of a resonator of the FBAR type with a micro-machined membranes of the prior art, following two various realizations, respectively with a supported membrane or with a cavity.
Figure 2B:
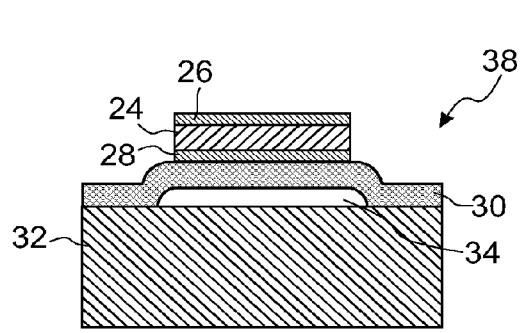

When the rejection filters of RF telemetry circuits of known implants implement BAW resonators, such resonators are components of the FBAR type presenting one of the two structures shown in FIGS. 2a and 2b. In the first structure, shown in FIG. 2a, the component 22 comprises a layer 24 of piezoelectric material excited by conducting electrodes 26, 28. When it is stressed, this materials transmits a portion of its energy to a membrane 30 made of a non-piezoelectric material, micro-machined on a massive substrate 32. Also, a part 34 of this massive substrate 32 has been locally eliminated, so as to form a cavity 34, that can be excited by the vibration of the exposed part 36 of the membrane. In the second alternative structure, shown in FIG. 2b, the substrate 32 is maintained intact, and the cavity 34 is formed by reserving an air interval between resonator 24 and the substrate 32. This interval is, for example, obtained by depositing a sacrificial layer between the resonator and the substrate, so that once that layer has been removed, the resonator 24 is hung upon the substrate.

As it can be easily understood, these structure are not easy to make and are fragile. Besides, the adjustment of the component's resonant frequency is strongly dependent upon the characteristics of the piezoelectric material, the thickness of the layers, dimensions of the resonant cavity and various mechanical constraints exerted onto the membrane, which has a tendency to be easily deformed and torn.

The starting point of the present invention is then choosing, for the band rejection filter, a resonator structure other than that of the FBAR resonators shown in FIGS. 2a and 2b.

More precisely, the present invention proposes to use, in a RF telemetry circuit for an active medical device, notably an active medical implant, a resonator of the SMR (Solidly Mounted Resonator) type, which is a different configuration of piezoelectric resonator, linked to the substrate, and not implementing any cavity nor any membrane.

Figure 3:
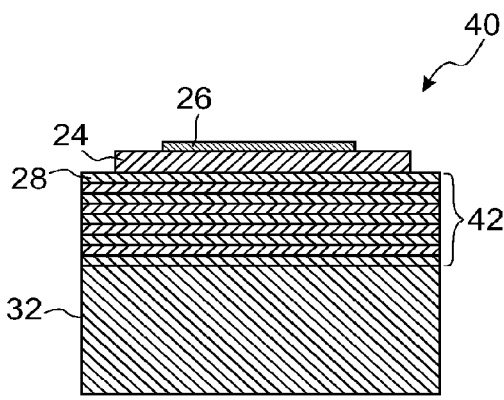
FIG. 3 shows the general configuration of a resonator of the SMR type with Bragg acoustic reflector associated with the present invention.

The general structure of a component of the SMR type is shown in FIG. 3. Such a component is a resonator 40 comprising a layer 24 of piezoelectric material, for example, Aluminum Nitride AlN, disposed between two metallic layers 26, 28 forming excitation electrodes, for example, made of molybdenum.

In order to prevent the acoustic wave to propagate and attenuate within, the resonant structure is acoustically insulated from substrate 32 by an interfaced structure comprising a stacking 42 of quarter-wave layers with very different acoustic impedances, alternately high and low, to realize a Bragg acoustic reflector. The layers constituting the stacking 42 are, for example, alternated layers of Silicon Nitride SiN and Silicon Oxycarbide SiOC, and their number can reach ten or twelve or even more. More details can be found in published US patent application US 2004/0140869 cited above, which explains the theory and electrical performances of such components.

This resonator has the advantage of being able to be realized on a very wide variety of substrates (the acoustic properties of the substrate having no importance) and also integrable to the global manufacturing process of the monolithic circuit to which the resonator will be associated.

Figure 4:
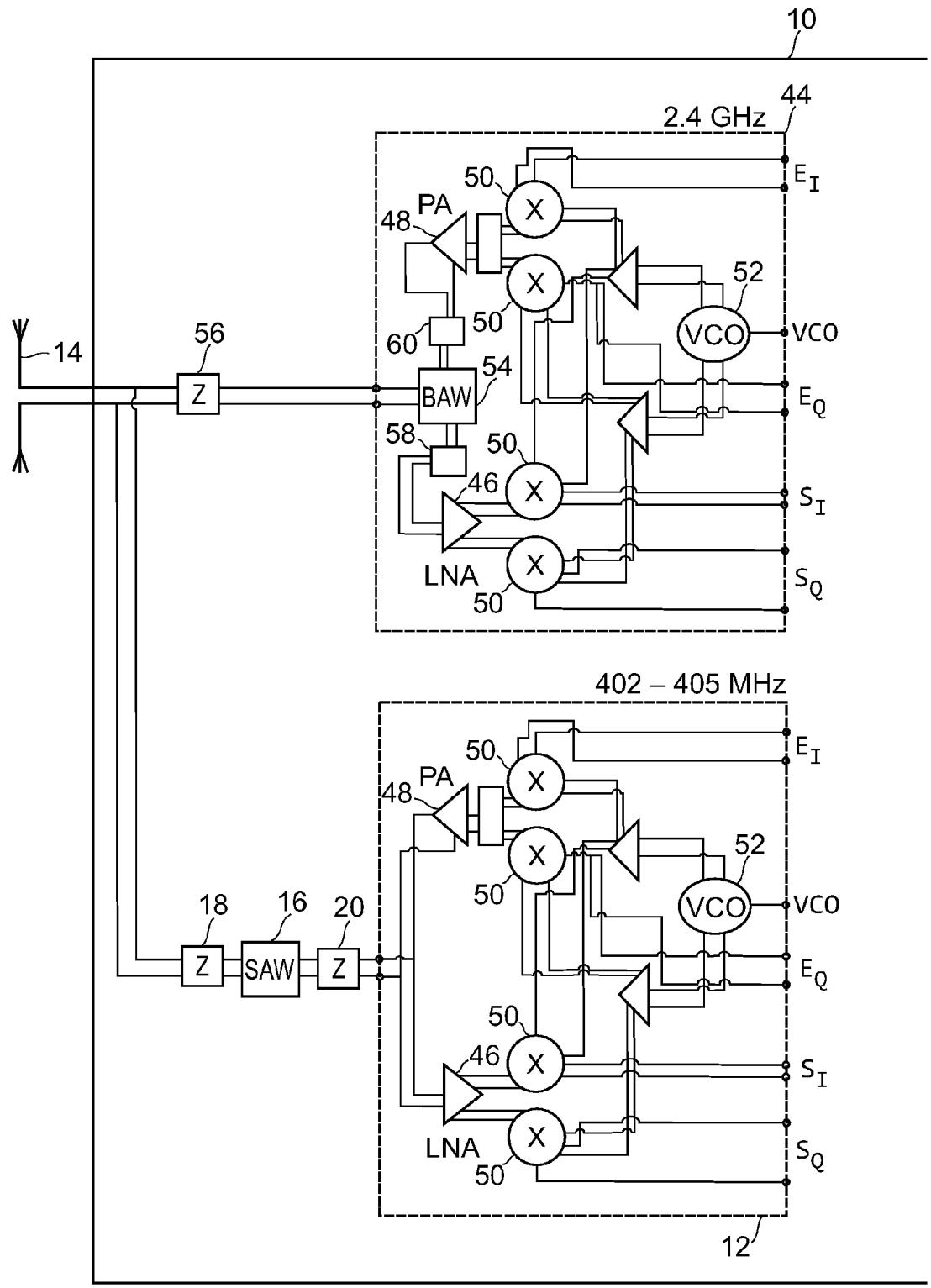
FIG. 4 shows RF telemetry transmitter/receiver circuits coupled to a common antenna, in an active device of the bi-band type in accordance with a preferred embodiment of the present invention.

FIG. 4 shows the configuration of a bi-band RF telemetry circuit using such a SMR resonator, for example, an RF telemetry circuit able to indifferently operate in the 402~405-MHz and 2.4-GHz bands. The RF telemetry circuit 10 comprises two respective transmitter/receiver stages 12, 44 operating in each of the two bands concerned. These circuits present a similar structure, with, on the receiver side, a low-noise amplifier LNA 46 and, on the transmitter side, a power amplifier PA 48. These receiver and transmitter amplifiers 46, 48 are coupled to various mixer stages 50 and to a voltage-controlled oscillator VCO 52. All these elements are controlled by input data signals in phase $E_I$ and in quadrature $E_Q$ and by an actuating signal of the VCO oscillator frequency, and deliver as output, data signals in phase $S_I$ and quadrature $S_Q$. The two transmitter/receiver circuits 12, 44 are coupled to a common antenna 14, for example, a dipole incorporated to the implant's case and linked by a bifilar symmetric line to each of the two transmitter/receiver circuits.

The circuit 12 operating in the 402~405-MHz band is, in a manner already known as such, coupled to the antenna 14 through a rejection filter 16 comprising a surface acoustic wave SAW resonator, with appropriate elements 18, 20 for impedance matching. The circuit 44 operating in the 2.4-GHz band is coupled to the antenna 14 through a rejection filter 54 comprising a BAW resonator of the SMR type, or a combination of a plurality of resonators of this type (see below). The coupling of filter 54 to the rest of the circuit is ensured by the respective elements 56 level with the antenna, 58 on the receiver side and 60 on the transmitter side.

The RF telemetry link can be indifferently established in the 402~405-MHz band or in the 2.4-GHz band. The choice of one band or the other for data transmission, can be advantageously performed automatically as a function of one or plural criteria, including, notably:

the level of the received signal in RSSI reception (Received Signal Strength Indicator) of the received RF signals, in one band or the other, by the implant (in the transmission direction programmer→implant) and by the programmer (in the transmission direction implant→programmer);

the maximum rate of data likely to be transmitted in one band or the other, and/or the workload of the different channels in one band and the other, so as to ensure having one free communication channel.

Every time an RF telemetry communication is initiated, a search is performed for the best band, and the data transmission is then performed in the chosen band. Advantageously, the electronic circuits of the band that has not been selected, are set in a low power consumption mode, so as to reduce the power consumed by the implant's battery.

Figure 5:
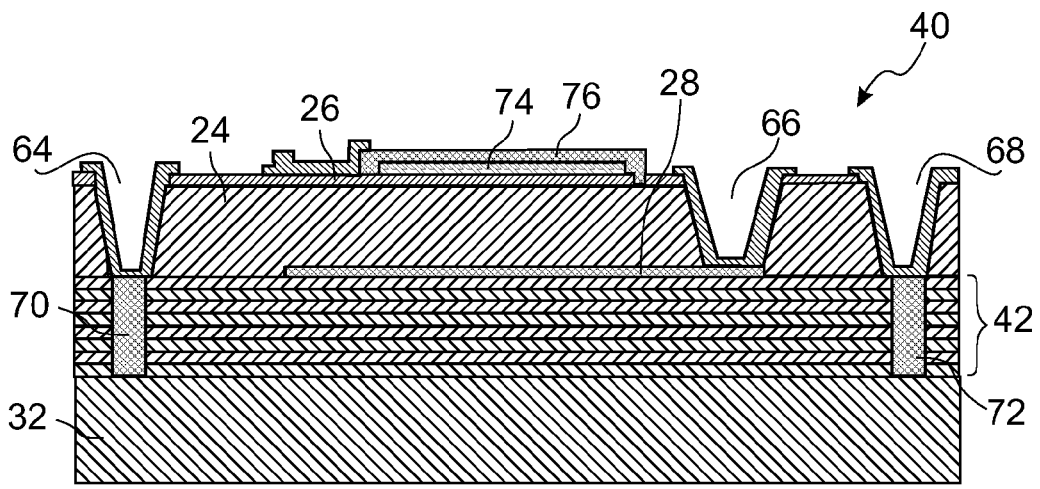
FIG. 5 shows details of a BAW resonator of the SMR type with acoustic Bragg reflector.

FIG. 5 describes in more detail the BAW resonator of the SMR type that is used (alone or in combination) as a band rejection filter for the device of the present invention.

Very advantageously, this resonator is formed along the same manufacturing process as the RF telemetry transmitter/receiver, i.e., the RF chip is a monolithic chip integrating its own resonator of the SMR type.

As explained above with reference to FIG. 3, the resonator 40 comprises a piezoelectric layer 24, for example, Aluminum Nitride AlN, disposed between two metallic excitation electrodes 26, 28, for example, Molybdenum. When an RF signal is applied between these two electrodes, a mechanical deformation is created in the material 24 and, for a predetermined frequency, the waves get strengthening and the component enters in resonance. The resonator is characterized by its free-running frequency, its coupling coefficient (representative of the insertion losses) and its quality factor. The free-running frequency is determined by various parameters such as the acoustic speed within the material, its Young module and the thicknesses of the various layers that compose it. Due to the mechanical behavior of the resonator, this resonator shall be insulated from the substrate 32 on which it is formed, so that the resonance can establish with a good coupling coefficient. In the case of a resonator of the SMR type, such insulation is realized through a stacking 42 of layers SiN/SiOC forming a Bragg acoustic reflector. The thickness of each layer is depending upon the resonator free-running frequency (quarter-wave) and the number of layers is calculated so as to optimize the final reflection, typically at least 99% of the acoustic signal being reflected. In order to realize the electrical connection between the excitation electrodes 26, 28 of the piezoelectric crystal and the different circuits of the chip, the layer 24 is dug out, for example, level with 64, 66, 68, and coated with a metallization layer, down to the vias such as 70, 72, formed through the stack 42 forming a Bragg reflector, in extremity areas located beyond the area of the piezoelectric layer 24 drawn to vibration by electrical stress of electrodes 26, 28.

Very advantageously, the resonator 40 comprises on its upper surface, a charge layer 74, for example in $SiO_2$, which is neutral from an electrical point of view, but which has the effect, due to its mass, to have an influence on the free-running frequency of the resonant structure. This layer allows, through a controlled selective material removal (for example, by erosion through the use of a laser or ion beam), to progressively remove a reduced quantity of material until the desired precise resonance frequency is obtained (a so-called trimming process). A passivation layer 76 of Silicon Nitride SiN protects the resonator structure once the resonator is tuned to the chosen free-running frequency.

Figure 6:
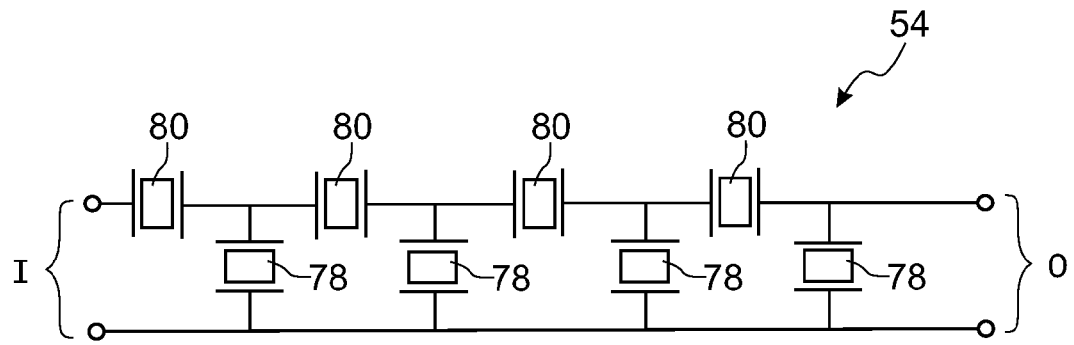
FIG. 6 shows the structure of an asymmetric rejection filter made based upon a combination of BAW resonators in a ladder configuration.
Figure 7:
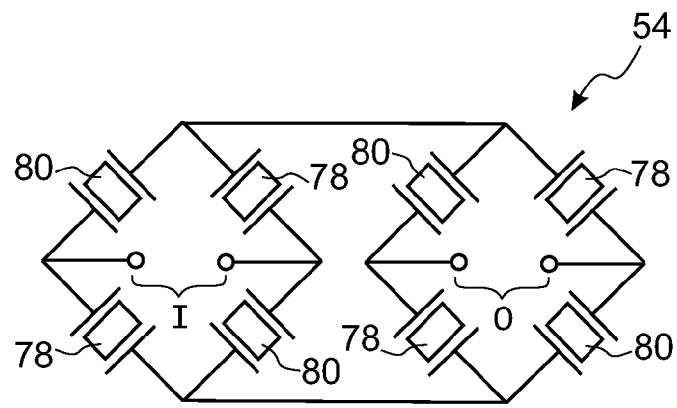
FIG. 7 shows the structure of a symmetric rejection filter, made based upon a combination of BAW resonators in a mesh configuration.

FIGS. 6 and 7 show two examples of combinations of BAW resonators of the SMR type, such as that which is described above, allowing to obtain a band rejection filter presenting the desired performances.

FIG. 6 shows a band rejection filter 54 with asymmetric input/output (I/O), the resonators being associated in a ladder configuration, for instance eight resonators, with four resonators in parallel 78 and four in series 80. The series and parallel resonators have slightly staggered frequencies, the band-pass of filter 54 being correlated to this staggering, with a resonant frequency of parallel resonators corresponding to the antiresonance frequency of the series resonators so as to minimize the insertion losses.

FIG. 7 show another possible configuration of four parallel resonators 78 and four series resonators 80 in a mesh configuration, adapted to the realization of a symmetric filter, for differential circuits.

The choice of an SMR as a resonator allows, taking into account the high technologic yield (few scraps), to realize in a monolithic manner, a band rejection filter comprising a plurality of associated resonators, typically a filter with four or eight resonators. Due to the multiplication of resonators within one single filter, a too high scrap rate per resonator (as with FBAR type resonators) would lead to a dramatic scrap for a filter comprising four or eight of such resonators, and would exclude an advanced integration.

Figure 8:
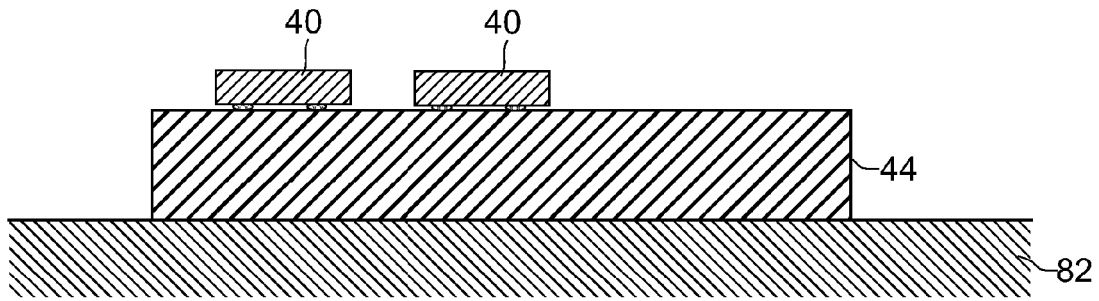
FIGS. 8, 9 and 10 show respectively three possible techniques of integration or bonding of SMR resonators on a RF telemetry circuit.
Figure 9:
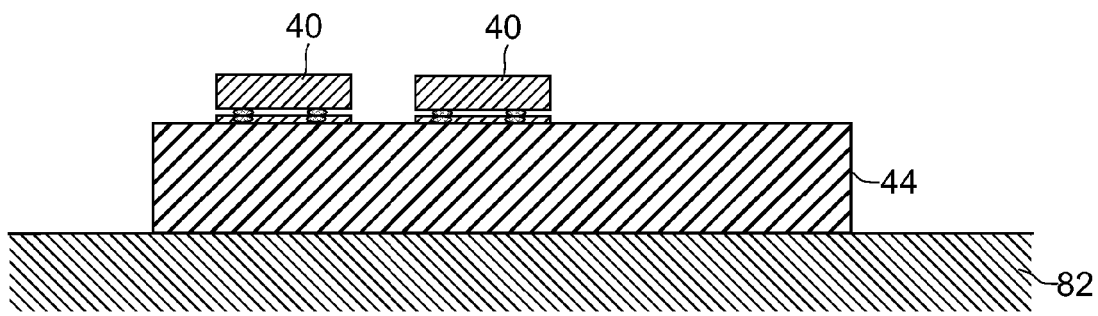
Figure 10:
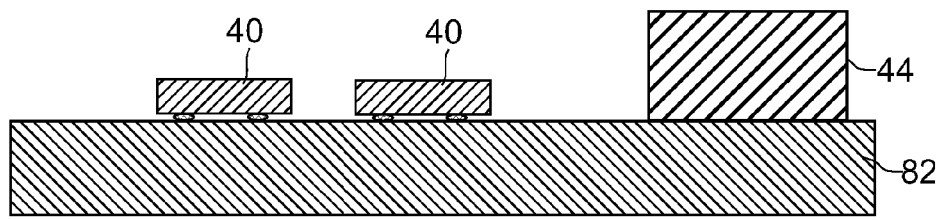

FIGS. 8 to 10 show alternative embodiments for associating resonators 40, notably combined together to realize a band rejection filter, to the monolithic chip 44 of the RF telemetry transmitter/receiver circuit, this chip being itself bonded on a hybrid circuit board 82 supporting and interconnecting the whole of the components, active and passive, of the medical device.

The first of these embodiments, shown in FIG. 8, realizes the various resonators 40 directly on the surface of the chip 44, in an integrated manner along the same step of the manufacturing process. More details on this integration technique are provided in U.S. Pat. No. 7,180,224 (assigned to ST Microelectronics S.A.), which describe an electronic component incorporating one or many associated resonators, realized in a monolithic manner.

The second of these embodiments, shown in FIG. 9, realizes the resonators in the form of autonomous discrete components that are bonded on the chip 44, for example, through a technique of the flip-chip type, or a similar technique. In this second embodiment, the manufacturing yield can be improved through a preliminary selection of the resonators before their bonding onto the chip 44.

The third of these embodiments, shown in FIG. 10, realizes the resonators 40 in the form of discrete components, but they are bonded on the hybrid circuit board 82 that also receives the circuit chip 44, and not to the chip 44.

One will note that the first two techniques are compatible with a stacking of the monolithic chips, where the chip of the RF telemetry transmitter/receiver circuits is for instance stacked upon the chip of the signal processing microcontroller, instead of being placed alongside it. That configuration has the advantage of saving available room for the electronic circuits within the implant's case. The integration of the resonators above the RF telemetry chip, which is superimposed to the microcontroller chip, only implies a global increase in thickness of a few tens of additional micrometers, negligible in terms of overall dimension.

Another advantage of this stacked configuration lies in that it allows to strongly reduce the impedances, notably the distributed inductances of the connecting wires, conductive pathways, bondings, etc. and prevents from having to retune the rejection filter resonator (or the combined different resonators that form this rejection filter) after bonding onto the chip.

One skilled in the art will appreciate that the present invention is not limited to the preferred embodiments discussed herein, which are provided for purposes of illustration of the invention, and not limitation.

I claim:

1. An active medical device, comprising:
   an RF antenna,
   a first RF telemetry transmitter/receiver having a first band rejection filter for coupling to the RF antenna, wherein the first RF telemetry transmitter/receiver operates in a first frequency band and wherein said first band rejection filler includes a volume acoustic waves BAW resonator of the SMR type with Bragg reflector insulation,
   a second RF telemetry transmitter/receiver having a second band rejection filter for coupling to the RF antenna, wherein the second RF telemetry transmitter/receiver operates in a second frequency band, and
   means for selecting, for RF communication, a frequency band of the first frequency band and the second frequency band,
   wherein the first RF telemetry transmitter/receiver and the second RF telemetry transmitter/receiver operate in at least two frequency bands selected from among the frequency bands of 401-402 MHz, 402-405 MHz, 405-406 MHz, 863-870 MHz, 902-928 MHz and 2.4 GHz or by a transmission of the UWB type.

2. The device of claim 1, wherein the RF antenna is common to the first RF telemetry transmitter/receiver and the second RF telemetry transmitter/receiver and coupled therewith through the first band rejection filter and the second band rejection filter and impedance matching elements.

3. The device of claim 1 further comprising means for evaluating performance of the first frequency band and the second frequency band, wherein the means for selecting selects the frequency band presenting the best performance.

4. The device of claim 1 further comprising:
   a hybrid circuit board and a chip, bonded on said board, of a monolithic circuit integrating said first RF telemetry transmitter/receiver, wherein the volume acoustic waves BAW resonator is directly integrated to the chip on a surface of the chip.

5. The device of claim 1 further comprising:
   a hybrid circuit board and a chip, bonded on said board, of a monolithic circuit integrating said first RF telemetry transmitter/receiver, wherein the volume acoustic waves BAW resonator is a discrete component, distinct from the chip and bonded on a surface of the chip.

6. The device of claim 5 wherein the volume acoustic waves BAW resonator is bonded on the surface of the chip through a flip-chip technique.

7. The device of claim 5 wherein the volume acoustic waves BAW resonator is bonded on the surface of the chip by a wire-bonding technique.

8. The device of claim 1 further comprising:
   a hybrid circuit board and a chip, bonded on said board, of a monolithic circuit integrating said first RF telemetry transmitter/receiver, wherein the volume acoustic waves BAW resonator is a discrete component, distinct from the chip and bonded on a surface of the hybrid circuit board.

9. The device of claim 1, wherein the volume acoustic waves BAW resonator is a tunable resonator comprising an erodable superficial charge layer.

10. The device of claim 1, wherein the first band rejection filter is a filter having a differential input and an output comprising a plurality of volume acoustic waves BAW resonators in a mesh configuration.

11. The device of claim 1, wherein the first band rejection filter is a filter having an asymmetric input and an output comprising a plurality of volume acoustic waves BAW resonators in a ladder configuration.

12. An active medical device, comprising:
    an RF antenna,
    a first RF telemetry transmitter/receiver having a first band rejection filter for coupling to the RF antenna, wherein the first RF telemetry transmitter/receiver operates in a first frequency band and wherein said first band rejection filter includes a volume acoustic waves BAW resonator of the SMR type with Bragg reflector insulation,
    a second RF telemetry transmitter/receiver having a second band rejection filter for coupling to the RF antenna, wherein the second RF telemetry transmitter/receiver operates in a second frequency band,
    means for selecting, for RF communication, a frequency band of the first frequency band and the second frequency band,
    means for evaluating performance of the first frequency band and the second frequency band, wherein the means for selecting selects the frequency band presenting the best performance, and
    means for commuting the transmitter/receiver operating within the band that was not selected towards a low power consumption mode.

* * * * *